US00PP23533P2

(12) United States Plant Patent
Hammett

(10) Patent No.: US PP23,533 P2
(45) Date of Patent: Apr. 16, 2013

(54) ***DIANTHUS* PLANT NAMED 'ANGEL OF DESIRE'**

(50) Latin Name: *Dianthus plumarius*
Varietal Denomination: Angel of Desire

(76) Inventor: Keith Richard William Hammett, Auckland (NZ)

( * ) Notice: Subject to any disclaimer, the term of this patent is extended or adjusted under 35 U.S.C. 154(b) by 35 days.

(21) Appl. No.: 13/068,017

(22) Filed: Apr. 29, 2011

(51) Int. Cl.
*A01H 5/00* (2006.01)
(52) U.S. Cl. ..... Plt./272
(58) Field of Classification Search ..... Plt./272
See application file for complete search history.

*Primary Examiner* — Susan McCormick Ewoldt
(74) *Attorney, Agent, or Firm* — Mark P. Bourgeois

(57) ABSTRACT

A new cultivar of *Dianthus* plant named 'Angel of Desire' that is characterized by a compact habit and a large number of flowers having red petals with a center white heart shaped area.

1 Drawing Sheet

Botanical classification: *Dianthus plumarius*.
Variety denomination: 'Angel of Desire'.

BACKGROUND OF THE INVENTION

The present invention relates to a new and distinct cultivar of *Dianthus* plant botanically known as *Dianthus plumarius* and hereinafter referred to by the cultivar name 'Angel of Desire'.

The new *Dianthus* is the product of a planned breeding program conducted by the inventor in Auckland, New Zealand. The objective of the breeding program is to create new *Dianthus* cultivars with attractive flower colors.

'Angel of Desire' originated from a crossing in 1989 of the female or seed parent *Dianthus plumarius* identified as 'Checkmate' (not patented) and the male or pollen parent *Dianthus plumarius* identified as 'Far Cry' (not patented). The resulting seeds were subsequently planted and grown. The cultivar 'Angel of Desire' was selected by the inventor in 2001 as a single plant within the progeny of the stated cross in a cultivated area of Auckland, New Zealand.

Asexual reproduction of the new cultivar 'Angel of Desire' first occurred by terminal cuttings in 2002 in Auckland, New Zealand. Since that time, under careful observation, the unique characteristics of the new cultivar have been uniform, stable and reproduced true to type in successive generations of asexual reproduction.

SUMMARY OF THE INVENTION

The following represent the distinguishing characteristics of the new *Dianthus* cultivar 'Angel of Desire'. These traits in combination distinguish 'Angel of Desire' as a new and distinct cultivar apart from other existing known varieties of *Dianthus*.

1. *Dianthus* 'Angel of Desire' exhibits a large number of flowers having red petals with a center white heart shaped marking.
2. *Dianthus* 'Angel of Desire' exhibits a compact habit.

'Angel of Desire' is distinguishable from the female or seed parent 'Checkmate' by the following characteristics:

1. 'Angel of Desire' has red flower petals with a center white heart shaped marking. In comparison, the flowers of 'Checkmate' are darker red in color with irregular shaped white markings.
2. 'Angel of Desire' has larger diameter flowers than the flowers of 'Checkmate'.

'Angel of Desire' is distinguishable from the male or pollen parent 'Far Cry' by the following characteristics:

1. 'Angel of Desire' has darker red flowers than the flowers of 'Far Cry'. In comparison, the flowers of 'Far Cry' are pink.
2. 'Angel of Desire' has a larger number of flowers when compared to the number of flowers on 'Far Cry'.

'Angel of Desire' is distinguishable from the co-pending plant patent application Ser. No. 13/068,015, *Dianthus* 'Angel of Peace' by the following characteristics:

1. 'Angel of Desire' has red flower petals with a center white heart shaped marking. In contrast, 'Angel of Peace' exhibits pink flower petals with a red base and white margins.

BRIEF DESCRIPTION OF THE DRAWING

The accompanying photograph illustrates the distinguishing traits of *Dianthus* 'Angel of Desire'. The plant in the photograph shows an overall view of an 8 month old plant. The photograph was taken using conventional techniques and although colors may appear different from actual colors due to light reflectance it is as accurate as possible by conventional photographic techniques.

BOTANICAL DESCRIPTION OF THE PLANT

The following is a detailed description of the new *Dianthus* cultivar named 'Angel of Desire'. Data was collected in Auckland, New Zealand, from 8 month old greenhouse grown plants in 10 cm. diameter containers. The time of year was Summer in the Southern Hemisphere and the temperature range was 18-26 degrees Centigrade during the day and 10-18 degrees Centigrade at night. The light level was natural light. No photoperiodic treatments or growth retardants were used. Color determinations are in accordance with The Royal Horticultural Society Colour Chart 2007 edition, except where general color terms of ordinary dictionary significance are used. The growing requirements are similar to the species. 'Angel of Desire' has not been tested under all possible conditions and phenotypic differences may be observed with variations in environmental, climatic, and cultural conditions, however, without any variance in genotype.

Botanical classification: *Dianthus plumarius* 'Angel of Desire'.

Annual or perennial: Perennial.

Parentage: 'Angel of Desire' is the product of the female or seed parent *Dianthus* 'Checkmate' and the male or pollen parent *Dianthus* 'Far Cry'.

Vigor: Moderate.

Growth habit: Upright.

Plant shape: Rounded.

Suitable container size: 10 cm. pots.

Height: 26 cm. in height.

Width: 24 cm. in width.

Low temperature tolerance: −15° Centigrade.

High temperature tolerance: 35° Centigrade.

Propagation: Terminal cuttings.

Crop time: Approximately 4 months.

Root system: Fine and fibrous.

Stem:

*Basal branching.*—Yes.
*Pinching.*—No.
*Lateral branch diameter.*—3 mm. in diameter.
*Lateral branch length.*—12 cm. in length.
*Internode length.*—1.0 cm.
*Stem shape.*—Round.
*Stem surface.*—Smooth.
*Stem strength.*—Strong.
*Stem color.*—135B.

Foliage:

*Leaf arrangement.*—Opposite.
*Compound or single.*—Single.
*Leaf shape.*—Linear.
*Leaf apex.*—Acute.
*Leaf base.*—Decurrent.
*Leaf length.*—6 cm. in length.
*Leaf width.*—4 mm. in width.
*Texture.*—Glaucous.
*Leaf margin.*—Entire.
*Young leaf color* (*upper surface*).—135B.
*Young leaf color* (*lower surface*).—135B.
*Mature leaf color* (*upper surface*).—135B.
*Mature leaf color* (*lower surface*).—135B.

Flower:

*Inflorescence arrangement.*—Cymose.
*Flower type.*—Salviform.
*Quantity of flowers and buds per plant.*—Average 55.
*Natural flowering season.*—Spring to Fall.
*Fragrance.*—Strong.
*Flower bud length.*—22 mm.
*Flower bud diameter.*—7 mm.
*Flower bud shape.*—Cylindrical.
*Bud color.*—138C.
*Flower aspect.*—Outward.
*Flower dimensions.*—38 mm. in diameter and 35 mm. in height.
*Flower longevity.*—10 to 12 days.
*Number of petals.*—5.
*Fused or unfused.*—Unfused.
*Petal texture.*—Smooth both sides.
*Petal arrangement.*—Apopetalous, overlapping.
*Petal shape.*—Obovate.
*Petal margin.*—Crenate-dentate.
*Petal apex.*—Rounded.
*Petal base.*—Fused.
*Petal length.*—30 mm.
*Petal width.*—26 mm.
*Petal color when opening* (*upper side*).—N74A with a center heart shaped area N155A.
*Petal color when opening* (*under side*).—N74A.
*Petal color fully opened* (*upper side*).—N74A with a center heart shaped area N155A.
*Petal color fully opened* (*under side*).—N74A.
*Self-cleaning or persistent.*—Persistant.

Calyx:

*Calyx dimensions.*—20 mm. in length and 8 mm. in diameter.

Sepals:

*Sepal shape.*—Lanceolate.
*Sepal arrangement.*—Fused at base.
*Number of sepals.*—5.
*Sepal margin.*—Entire.
*Sepal apex.*—Rounded.
*Sepal base.*—Fused.
*Sepal dimensions.*—16 mm. in length and 5 mm. in width.
*Young sepal color* (*upper side*).—133B.
*Young sepal color* (*under side*).—133B.
*Mature sepal color* (*upper side*).—133B.
*Mature sepal color* (*under side*).—133B.

Peduncle:

*Peduncle dimensions.*—16 cm. in length and 3 mm. in diameter.
*Peduncle angle.*—30 degrees from vertical.
*Peduncle strength.*—Moderate.
*Peduncle color.*—135B.

Reproduction organs:

*Stamen number.*—3 to 5.
*Anther shape.*—Oval, dorsifixed.
*Anther size.*—2 mm. in length and 1 mm. in width.
*Anther color.*—155C.
*Amount of pollen.*—Low.
*Pistil number.*—1.
*Pistil length.*—28 mm.
*Stigma shape.*—Round.
*Stigma color.*—144A.
*Style length.*—20 mm.
*Style color.*—145C.
*Ovary color.*—144C.

Fruit and seed: Fruit and seed production has not been observed.

Disease and pest resistance: Disease and pest resistance has not been observed.

It is claimed:

1. A new and distinct variety of *Dianthus* plant named 'Angel of Desire' as described and illustrated.

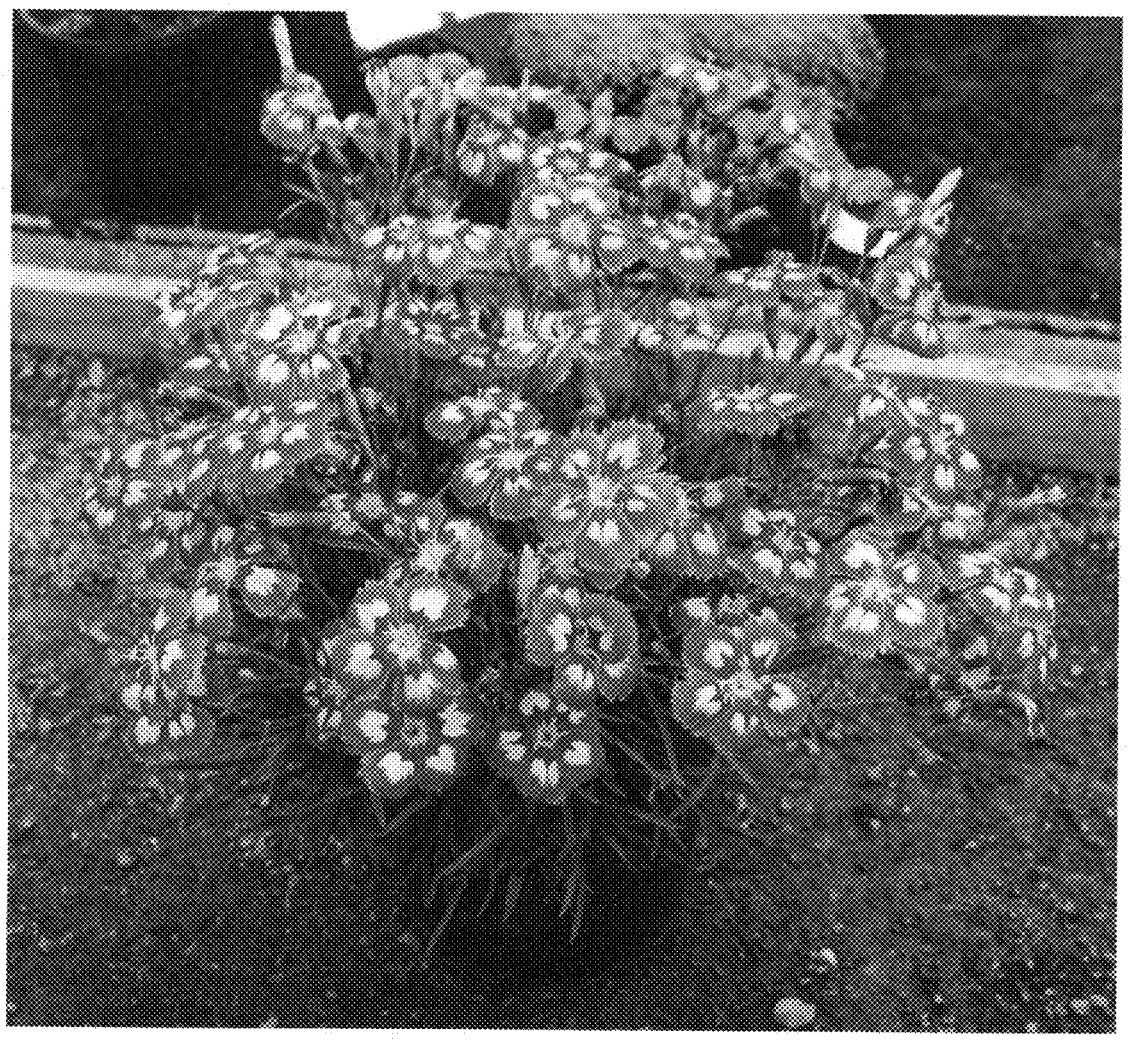

* * * * *